US012758427B2

(12) United States Patent
Fu et al.

(10) Patent No.: US 12,758,427 B2
(45) Date of Patent: Oct. 13, 2026

(54) FEMTOSECOND LASER SYSTEM AND METHOD FOR PRESBYOPIA CORRECTION

(71) Applicant: AMO Development, LLC, Irvine, CA (US)

(72) Inventors: Hong Fu, Pleasanton, CA (US); Mohammad Saidur Rahaman, San Jose, CA (US); Tobin Island, Santa Cruz, CA (US); Xiao-Yu Song, Jacksonville, FL (US)

(73) Assignee: AMO Development, LLC, Irvine, CA (US)

( * ) Notice: Subject to any disclaimer, the term of this patent is extended or adjusted under 35 U.S.C. 154(b) by 152 days.

(21) Appl. No.: 18/927,793

(22) Filed: Oct. 25, 2024

(65) Prior Publication Data

US 2026/0115047 A1 Apr. 30, 2026

(51) Int. Cl.
*A61F 9/008* (2006.01)

(52) U.S. Cl.
CPC ........ *A61F 9/00838* (2013.01); *A61F 9/0084* (2013.01); *A61F 2009/00851* (2013.01);
(Continued)

(58) Field of Classification Search
CPC ................ A61F 9/00838; A61F 9/0084; A61F 2009/00851; A61F 2009/0087;
(Continued)

(56) References Cited

U.S. PATENT DOCUMENTS 6,322,556 B1 11/2001 Gwon et al.
6,745,775 B2 6/2004 Lin
(Continued)

FOREIGN PATENT DOCUMENTS

CN 201216684 Y 4/2009
CN 113101049 A 7/2021
(Continued)

OTHER PUBLICATIONS

Kermani et al., "Softening the Presbyopic Lens with a Femtosecond Laser", Eyenet, pp. 31-33, Sep. 2014.
(Continued)

*Primary Examiner* — Jonathan T Kuo

(57) ABSTRACT

A method for treating presbyopia of a crystalline lens using a femtosecond laser system, operated in a parameter regime characterized by extremely short pulse duration (below 100 fs) and low pulse energy (sub-μJ) of the pulses delivered to the lens tissue. The laser beam has a small focal volume in the tissue that is achieved by the short spatial pulse length, rather than defined by the large depth of focus resulting from the low numerical aperture of the laser beam. The laser energy density within the small focal volume (below 50 $\mu m^3$) is sufficiently high to induce optical breakdown of the tissue, which reduces the Young's modulus of the lens to improve accommodation, thereby reducing presbyopia. Meanwhile, the total pulse energy in the focal volume is sufficiently low, resulting in small cavitation bubbles, which reduce light scattering and other damage or undesirable effects in the treated lens tissue.

31 Claims, 6 Drawing Sheets

(52) U.S. Cl.
CPC ................. *A61F 2009/0087* (2013.01); *A61F 2009/00895* (2013.01); *A61F 2009/00897* (2013.01)

(58) Field of Classification Search
CPC ........ A61F 2009/00895; A61F 9/00825; A61F 9/008–2009/00897
See application file for complete search history.

(56) References Cited

U.S. PATENT DOCUMENTS 6,923,955 B2 8/2005 Till et al.
7,275,545 B2 10/2007 Lin
7,351,241 B2 4/2008 Bendett et al.
RE40,420 E 7/2008 Dick et al.
7,655,002 B2 2/2010 Myers
7,717,908 B2 5/2010 Ruiz et al.
8,057,541 B2 11/2011 Dishler et al.
8,182,471 B2 5/2012 Yee
8,186,357 B2 5/2012 Lubatschowski et al.
8,246,609 B2 8/2012 Zickler et al.
8,262,646 B2 9/2012 Frey et al.
8,377,048 B2 2/2013 Bille
8,409,181 B2 4/2013 Bor
8,435,233 B2 5/2013 Singh
8,475,438 B2 7/2013 Larsen
8,496,651 B2 7/2013 Ruiz et al.
8,556,886 B2 10/2013 Youssefi
8,596,281 B2 12/2013 Suckewer et al.
8,597,283 B2 12/2013 Bischoff et al.
8,632,527 B2 1/2014 Bischoff et al.
8,647,334 B2 2/2014 McArdle et al.
8,663,208 B2 3/2014 Bor
8,685,006 B2 4/2014 Wiechmann et al.
8,764,736 B2 7/2014 Kurtz
8,911,431 B2 12/2014 Reich et al.
8,991,401 B2 3/2015 McArdle et al.
9,125,735 B2 9/2015 De Juan, Jr et al.
9,161,857 B2 10/2015 Mordaunt et al.
9,168,175 B2 10/2015 Feingold
9,301,806 B2 4/2016 Esposito
9,345,549 B2 5/2016 Hickenbotham
9,393,154 B2 7/2016 Myers
9,572,716 B2 2/2017 Russmann et al.
9,649,224 B2 5/2017 McArdle et al.
9,681,984 B2 6/2017 Peyman
9,877,870 B2 1/2018 Dick et al.
10,058,453 B2 8/2018 Seiler et al.
10,092,393 B2 10/2018 Muller
10,123,906 B2 11/2018 Bergt et al.
10,130,511 B2 11/2018 Dantus
10,166,073 B2 1/2019 Bischoff et al.
10,251,781 B2 4/2019 Ho et al.
10,292,865 B2 5/2019 Jester et al.
10,292,867 B2 5/2019 Dick et al.
10,383,768 B2 8/2019 Esposito
10,449,089 B2 10/2019 Gross et al.
10,548,771 B2 2/2020 Coleman et al.
10,603,216 B2 3/2020 Kurtz et al.
10,675,183 B2 6/2020 Kahra et al.
10,716,705 B2 7/2020 Fu
10,736,731 B2 8/2020 Anderson et al.
10,758,413 B2 9/2020 Telandro
10,779,988 B2 9/2020 Fu et al.
10,799,392 B2 * 10/2020 Lubatschowski ....... A61F 9/008
10,932,901 B2 3/2021 Zheleznyak et al.
10,952,608 B2 3/2021 Yoo et al.
10,952,900 B2 3/2021 Muller
11,033,432 B2 6/2021 Papastathopoulos et al.
11,039,957 B2 6/2021 Sluyterman van Langeweyde et al.
11,234,864 B2 2/2022 Romano et al.
11,253,397 B2 2/2022 Bischoff et al.
11,259,914 B2 3/2022 Peyman
11,272,986 B2 3/2022 Dishler et al.
11,311,418 B2 4/2022 Dick et al.
11,351,062 B2 6/2022 Bernard et al.
11,357,667 B2 6/2022 Bischoff et al.
11,382,795 B2 7/2022 Zheleznyak et al.
11,406,535 B2 8/2022 Lubatschowski
11,504,277 B2 11/2022 Baubeau
11,540,947 B2 1/2023 Malek Tabrizi et al.
11,559,390 B2 1/2023 Muller et al.
11,590,026 B2 2/2023 Arba-Mosquera et al.
11,602,457 B2 3/2023 Bischoff et al.
11,607,339 B2 3/2023 Teuma et al.
11,642,244 B2 5/2023 Adler et al.
11,654,054 B2 5/2023 Raksi
2004/0059320 A1 3/2004 Telandro et al.
2004/0078030 A1 4/2004 Lin
2005/0165387 A1 7/2005 Lubatschowski et al.
2006/0064077 A1 3/2006 Peyman
2006/0264917 A1 11/2006 Tuan et al.
2007/0203478 A1 8/2007 Herekar
2007/0235043 A1 10/2007 Baikoff
2009/0137991 A1 5/2009 Kurtz
2009/0216218 A1 8/2009 Somani et al.
2009/0234336 A1 9/2009 Chernyak et al.
2009/0281530 A1 11/2009 Korn
2010/0191229 A1 7/2010 Bille et al.
2011/0118712 A1 5/2011 Lubatschowski et al.
2011/0202114 A1 8/2011 Kessel et al.
2012/0016350 A1 1/2012 Myers et al.
2012/0172852 A1 * 7/2012 Lubatschowski ....... A61F 9/008 606/4
2013/0053952 A1 2/2013 Jun et al.
2014/0107631 A1 4/2014 Ferrari
2014/0155871 A1 6/2014 Cumming
2015/0025510 A1 1/2015 Vogler et al.
2015/0157505 A1 * 6/2015 Neev .................. A61F 9/00814 606/5
2015/0250650 A1 9/2015 Mosquera et al.
2015/0305927 A1 10/2015 Walter
2016/0374857 A1 12/2016 Fu et al.
2017/0143543 A1 5/2017 Mcardle
2017/0319329 A1 11/2017 Muller et al.
2018/0214306 A1 8/2018 Chassagne et al.
2019/0240003 A1 8/2019 Klopotek
2020/0038239 A1 2/2020 Mikula et al.
2020/0261273 A1 8/2020 Arba-Mosquera et al.
2021/0259881 A1 8/2021 Gray et al.
2021/0369500 A1 12/2021 Hegedus et al.
2022/0183885 A1 6/2022 Bor et al.
2023/0086252 A1 3/2023 Sweeney
2023/0129891 A1 4/2023 Arba Mosquera et al.
2023/0165718 A1 6/2023 Glazier
2023/0172704 A1 6/2023 Eisenbach et al.
2023/0172756 A1 6/2023 Arba Mosquera
2023/0181369 A1 6/2023 Lopez et al.
2023/0404806 A1 12/2023 Romano et al.

FOREIGN PATENT DOCUMENTS

DE 102008049401 A1 4/2010
DE 102009009382 A1 8/2010
DE 102017122164 A1 3/2019
DE 102019115495 A1 12/2020
DE 102019118315 A1 1/2021
DE 102020114791 A1 12/2021
EP 1981426 B1 3/2020
WO 2002078585 A2 10/2002
WO 02094129 A2 11/2002
WO 2008150291 A1 12/2008
WO 2010031395 A1 3/2010
WO 2010046987 A1 4/2010
WO 2014018104 A1 1/2014
WO 2014071408 A1 5/2014
WO 2022207900 A1 10/2022

(56) References Cited

FOREIGN PATENT DOCUMENTS

| | | | |
|---|---|---|---|
| WO | 2022272107 | A1 | 12/2022 |
| WO | 2023041623 | A1 | 3/2023 |

OTHER PUBLICATIONS

Kermani et al., Clinical Study on Femtosecond Laser Restoration of Accommodation, Graefe's Archive for Clinical and Experimental Ophthalmology, vol. 262, pp. 991-993, 2024.

Krueger et al., "Ultrashort-Pulse Lasers Treating the Crystalline Lens: Will They Cause Vision-threatening Cataract? (An American Ophthalmological Society Thesis)", Transactions of the American Ophthalmological Society, vol. 110, pp. 130-165, Dec. 2012.

Lubatschowski et al., "Fs-Lentotomy: Presbyopia Reversal by Generating Gliding Planes Inside the Crystalline Lens", Klinische Monatsblätter für Augenheilkunde, vol. 226, No. 12, pp. 984-990, Dec. 2009.

Myers et al., "Novel Approaches to Correction of Presbyopia with Laser Modification of the Crystalline Lens", Journal of refractive surgery, vol. 14, No. 2, pp. 136-139, Mar. 1, 1998.

* cited by examiner

| λ (um) | Maximum Focal Volume $V_{max}$ ($\mu m^3$) | | | |
|---|---|---|---|---|
| 1.03 | 50 | 40 | 30 | 20 |
| NA | $\tau_{max}$ for V = 50 um^3 | $\tau_{max}$ for V = 40 um^3 | $\tau_{max}$ for V = 30 um^3 | $\tau_{max}$ for V = 20 um^3 |
| 0.100 | 13 | 10 | 8 | 5 |
| 0.110 | 15 | 12 | 9 | 6 |
| 0.120 | 18 | 15 | 11 | 7 |
| 0.130 | 21 | 17 | 13 | 9 |
| 0.140 | 25 | 20 | 15 | 10 |
| 0.150 | 29 | 23 | 17 | 11 |
| 0.160 | 32 | 26 | 19 | 13 |
| 0.170 | 37 | 29 | 22 | 15 |
| 0.180 | 41 | 33 | 25 | 16 |
| 0.190 | 46 | 37 | 27 | 18 |
| 0.200 | 51 | 41 | 30 | 20 |
| 0.210 | 56 | 45 | 34 | 22 |
| 0.220 | 61 | 49 | 37 | 25 |
| 0.230 | 67 | 54 | 40 | 27 |
| 0.240 | 73 | 58 | 44 | 29 |
| 0.250 | 79 | 63 | 48 | 32 |
| 0.260 | 86 | 69 | 51 | 34 |
| 0.270 | 92 | 74 | 55 | 37 |
| 0.280 | 99 | 80 | 60 | 40 |
| 0.290 | 107 | 85 | 64 | 43 |
| 0.300 | 114 | 91 | 68 | 46 |

FEMTOSECOND LASER SYSTEM AND METHOD FOR PRESBYOPIA CORRECTION

BACKGROUND OF THE INVENTION

This invention relates to ophthalmic laser surgery systems and methods, and in particular, it relates to a system and method for using a femtosecond pulsed laser beam to treat the crystalline lens to correct presbyopia.

People over the age of forty are progressively developing presbyopia and losing accommodation for near vision. Around 25% of total population (1.8 billion globally) are currently affected. Presbyopia is the result of reduced accommodation of the crystalline lens, caused by an increase of the Young's modulus, i.e., reduction of elasticity, of the lens tissue. The main changes that occur with aging include: reduced diffusion of water from the outside to the inside of the lens and from its cortical to its nuclear zone; crystalline change due to the accumulation of high molecular weight aggregates and insoluble proteins; production of advanced glycation end products (AGEs), lipid accumulation, reduction of reduced glutathione content and destruction of ascorbic acid, etc. Current solutions for correcting presbyopia include wearing reading glasses, progressive glasses, multifocal glasses, multifocal contact lenses, implant multifocal/Presbyopia-Correcting IOL, and pharmaceutical eye drops with temporary effect.

It has been proposed that presbyopia may be treated by delivering laser pulses into the crystalline lens to change the lens's elasticity so as to improve accommodation. For example, R Myers and R Krueger, Novel Approaches to Correction of Presbyopia with Laser Modification of the Crystalline Lens. J. Refract. Surg. (1998) 14, 136-139 ("Myers 1998") proposes using pulsed laser beam to treat presbyopia. Lubartschowski et al., fs-Lentotomy: Presbyopia Reversal by Generating Gliding Planes inside the Crystalline Lens. Klin. Monatsbl Augenheilkd 2009; 226:984-990 ("Lubartschowski 2009") demonstrated preliminary preclinical feasibility, using a laser beam of 1.0 to 1.6 μJ pulse energy and 125 to 308 fs pulse duration.

R Krueger et al. conducted several human clinical studies by 2014 with fewer than 200 eyes. They first used 25-45 μJ pulse energy and 10 ps pulse duration, then used 10 μJ pulse energy and 10 ps pulse duration. They concluded that "The bottom line is that some results are promising, but reproducible, consistent efficacy has not yet been demonstrated." See R Krueger et al., Ultrashort-Pulse Lasers Treating the Crystalline Lens: Will They Cause Vision-Threatening Cataract? Trans. AM Ophthalmol Soc 2012; 110:130-165 ("Krueger 2012"); and O Kermani, R Krueger, S Shah, Softening the Presbyopic Lens with a Femtosecond Laser, Eyenet, (2014) September, 31-33 ("Kermani 2014").

Another study of laser presbyopia treatment reported lesion scars for the treated tissue after 12 months, and reported improved accommodation up to 2D and unwanted hyperopia and large refraction variations. See O Kermani, G Gerten, U Oberheide, H Lubatschowski, Clinical study on femtosecond laser restoration of accommodation, Graefe's Archive for Clinical and Experimental Ophthalmology, https://doi.org/10.1007/s00417-023-06188-w, Received: 10 May 2023/Revised: 17 Jul. 2023/Accepted: 21 Jul. 2023 (Kermani 2023).

Using pulsed laser beam to treat presbyopia is also described in various patent documents, including, for example, U.S. Pat. Nos. 10,799,392, 11,607,339, 8,186,357, 8,475,438, 11,311,418, 7,655,002, 8,262,646, and 7,351,241, and U.S. Pat. Appl. Pub. No. 20110202114.

SUMMARY OF THE INVENTION

The present invention is directed to a laser presbyopia treatment method and related ophthalmic laser system that substantially obviate one or more of the problems due to limitations and disadvantages of the related art.

To treat the lens tissue to improve its elasticity, the laser energy density (laser energy per unit volume) delivered into the lens tissue must be above the laser-induced optical breakdown (LIOB) threshold (also referred to as the plasma threshold). In the plasma region, i.e. the region where laser energy density is above the plasma threshold, the tissue will be vaporized due to the high temperature of the plasma; in the vicinity of the plasma, the tissue will be cut or separated mechanically by the plasma-induced cavitation bubble and shockwave. To reduce light scattering in the treated lens tissue and avoid other damage or undesirable effects such as optical opacity and unfavorable tissue regrowth, the size of the cavitation bubble should be as small as possible, which means the total energy within the plasma region should be as low as possible, because the total energy determines the cavitation bubble size. On the other hand, laser treatment of the crystalline lens requires a relatively low numerical aperture (NA) of the laser beam due to pupil shadowing effect; such a relatively low numerical aperture results in a relatively large focal volume of the laser beam, which increases the total pulse energy required in order to achieve laser-induced optical breakdown.

The ophthalmic laser system design and operation regime according to embodiments of the present invention are guided by careful considerations of these factors to facilitate successful laser presbyopia treatment. To summarize briefly, a key enabling feature according to embodiments of the present invention is to operate the femtosecond laser in a new parameter regime which uses extremely short femtosecond laser pulses such that the spatial pulse length, as delivered in the lens tissue, is shorter than the depth of focus of the beam delivery optics. Under such conditions, the focal volume can be reduced to below the focal volume determined by the numerical aperture of the optical system. As a result, the pulse energy for cutting the fibers and the tissues of the crystalline lens can be reduced to sub-μJ. Such ultra-low pulse energy can reduce light scattering and other damage or undesirable effects in the treated lens tissue.

Additional features and advantages of the invention will be set forth in the descriptions that follow and in part will be apparent from the description, or may be learned by practice of the invention. The objectives and other advantages of the invention will be realized and attained by the structure particularly pointed out in the written description and claims thereof as well as the appended drawings.

To achieve the above objects, the present invention provides a laser treatment method for treating presbyopia of a crystalline lens of a patient's eye, which includes: generating a pulsed laser beam comprising a plurality of laser pulses; focusing the pulsed laser beam to a beam focus inside the lens, wherein a numerical aperture NA of the laser beam is between 0.125 and 0.20, and a focal volume of the beam focus within the lens is less than 50 $\mu m^3$, wherein the focal volume is defined by a diameter of the beam focus at a focal plane and a spatial pulse length of the laser pulses in the lens; and scanning the pulsed laser beam in the lens according to a treatment pattern, to induce optical breakdown of lens tissue at the beam focus to reduce Young's modulus of the tissue.

In some embodiments, the focal volume of the beam focus within the lens is greater than 20 $\mu m^3$. In some embodiments, generating the pulsed laser beam includes generating an original pulsed laser beam and performing group velocity dispersion pre-compensation of the original pulsed laser beam. In some embodiments, when scanning the pulsed laser beam in the lens according to a treatment pattern, the pulsed laser beam has a first numerical aperture when treating an anterior and center portion of the lens, and has a second numerical aperture which is lower than the first numerical aperture when treating a posterior and peripheral portion of the lens.

In some embodiments, scanning the pulsed laser beam in the lens according to a treatment pattern includes scanning the pulsed laser beam at oblique incidence angles in the lens. In some embodiments, the pulsed laser beam focused inside the lens has a pulse duration of 8 fs to 51 fs and has a photodisruption threshold pulse energy of 36 nJ to 90 nJ. In some embodiments, generating the pulsed laser beam includes generating an original pulsed laser beam having an original pulse energy above 20 μJ, and attenuating the original pulsed laser beam using a two-stage polarization attenuator.

In another aspect, the present invention provides a laser treatment method for treating presbyopia of a crystalline lens of a patient's eye, which includes: generating a pulsed laser beam comprising a plurality of laser pulses; focusing the pulsed laser beam into a beam focus inside the lens, wherein a numerical aperture NA of the laser beam is between 0.125 and 0.2, a pulse duration $\tau$ of the laser pulses in the lens is from 8 fs to 51 fs, and a photodisruption threshold pulse energy $E_0$ in the lens is from 36 nJ to 90 nJ; and scanning the pulsed laser beam in the lens according to a treatment pattern, to cause laser-induced optical breakdown of lens tissue at the beam focus to reduce Young's modulus of the tissue.

In some embodiments, the pulse duration r and the photodisruption threshold pulse energy $E_0$ satisfy the relationship: $\tau \leq 3.157\ n \cdot NA^2 \cdot E_0/(c \cdot \lambda^2)$, where n is a refractive index of the tissue, c is the speed of light (c=0.3 μm/fs), and $\lambda$ (in μm) is a wavelength of the pulsed laser beam. In some embodiments, generating the pulsed laser beam includes generating an original pulsed laser beam having a pulse duration of less than 200 fs, and performing group velocity dispersion pre-compensation for the original pulsed laser beam so that the pulsed laser beam focused to the lens has a pulse duration of less than 200 fs.

In some embodiments, the when scanning the pulsed laser beam in the lens according to a treatment pattern, the pulsed laser beam has a first numerical aperture when treating an anterior and center portion of the lens, and has a second numerical aperture which is lower than the first numerical aperture when treating a posterior and peripheral portion of the lens. In some embodiments, scanning the pulsed laser beam in the lens according to a treatment pattern includes scanning the pulsed laser beam at oblique incidence angles in the lens. In some embodiments, generating the pulsed laser beam includes generating an original pulsed laser beam having an original pulse energy above 20 μJ, and attenuating the original pulsed laser beam using a two-stage polarization attenuator.

In another aspect, the present invention provides an ophthalmic laser surgery system for treating presbyopia of a crystalline lens of a patient's eye, the system including: a laser source configured to generate a pulsed laser beam comprising a plurality of laser pulses; and a laser beam delivery optical system configured to focus the pulsed laser beam into a beam focus inside the lens and to scan the pulsed laser beam in the lens according to a treatment pattern, wherein a numerical aperture NA of the laser beam is between 0.125 and 0.2, and a focal volume of the beam focus within the lens is less than 50 $\mu m^3$, wherein the focal volume is defined by a diameter of the beam focus at a focal plane and a spatial pulse length of the laser pulses in the lens, and wherein the pulsed laser beam induces optical breakdown of lens tissue at the beam focus to reduce Young's modulus of the tissue.

In some embodiments, the pulsed laser beam focused inside the lens has a pulse duration of 8 fs to 51 fs and a photodisruption threshold pulse energy of 36 nJ to 90 nJ. In some embodiments, the laser source includes a femtosecond laser, and a pulse picker configured to perform fast-blanking of laser pulses generated by the femtosecond laser. In some embodiments, the laser source further includes a pulse compressor configured to generate an original pulsed laser beam having a pulse duration of less than 200 fs, and a group velocity dispersion pre-compensation device configure to perform group velocity dispersion pre-compensation of the original pulsed laser beam so that the pulsed laser beam focused to the lens has a pulse duration of less than 200 fs.

In some embodiments, the laser beam delivery optical system includes two-stage polarization attenuator, comprising a first attenuator, which is set to a fixed value of attenuation, and a second, variable attenuator, and the second attenuator including a half-wave plate and a polarization beam splitter. In some embodiments, the laser beam delivery optical system includes a beamsplitter configured to direct a portion of a laser beam reflected from the lens tissue to a light detector to detect photodisruption of the tissue.

In some embodiments, the laser beam delivery optical system includes a variable aperture configured to adjust a numerical aperture of the pulsed laser beam, and wherein the laser beam delivery optical system is configured to scan the pulsed laser beam having a first numerical aperture in an anterior and center portion of the lens, and to scan the pulsed laser beam having a second numerical aperture which is lower than the first numerical aperture in a posterior and peripheral portion of the lens. In some embodiments, the laser beam delivery optical system is configured to scan the pulsed laser beam at oblique incidence angles in the lens. In some embodiments, the system further includes an optical coherence tomography subsystem configured to generate images of the lens tissue, and wherein the laser beam delivery optical system includes a beam combiner configured to combine an OCT sample beam and the pulsed laser beam into a common optical path.

In another aspect, the present invention provides an ophthalmic laser surgery system for treating presbyopia of a crystalline lens of a patient's eye, the system including: a laser source configured to generate a pulsed laser beam comprising a plurality of laser pulses; and a laser beam delivery optical system configured to focus the pulsed laser beam into a beam focus inside the lens and to scan the pulsed laser beam in the lens according to a treatment pattern, herein a numerical aperture NA of the laser beam is between 0.125 and 0.2, a pulse duration $\tau$ of the laser pulses in the lens is from 8 fs to 51 fs, and a photodisruption threshold pulse energy $E_0$ of the laser pulses in the lens is from 36 nJ to 90 nJ, and wherein the pulsed laser beam induces optical breakdown of lens tissue at the beam focus to reduce Young's modulus of the tissue.

In some embodiments, the pulse duration r and the pulse energy E satisfy a relationship: $\tau \leq 3.157\ n \cdot NA^2 \cdot E/(c \cdot \lambda^2)$, where n is a refractive index of the tissue, c is the speed of light (c=0.3 μm/fs), and $\lambda$ (in unit μm) is a wavelength of the pulsed laser beam. In some embodiments, the laser source includes a femtosecond laser, and a pulse picker configured to perform fast-blanking of laser pulses generated by the femtosecond laser. In some embodiments, the laser source further includes a pulse compressor configured to generate an original pulsed laser beam having a pulse duration of less than 200 fs, and a group velocity dispersion pre-compensation device configure to perform group velocity dispersion pre-compensation of the original pulsed laser beam so that the pulsed laser beam focused to the lens has a pulse duration of less than 200 fs.

In some embodiments, the laser beam delivery optical system includes two-stage polarization attenuator, comprising a first attenuator, which is set to a fixed attenuation, and a second, variable attenuator, the second attenuator including a half-wave plate and a polarization beam splitter. In some embodiments, the laser beam delivery optical system includes a beamsplitter configured to direct a portion of a laser beam reflected from the lens tissue to a light detector to detect photodisruption of the tissue.

In some embodiments, the laser beam delivery optical system includes a variable aperture configured to adjust a numerical aperture of the pulsed laser beam, and wherein the laser beam delivery optical system is configured to scan a pulsed laser beam having a first numerical aperture in an anterior and center portion of the lens, and to scan a pulsed laser beam having a second numerical aperture which is lower than the first numerical aperture in a posterior and peripheral portion of the lens. In some embodiments, the laser beam delivery optical system is configured to scan the pulsed laser beam at oblique incidence angles in the lens. In some embodiments, the system further includes an optical coherence tomography subsystem configured to generate images of the lens tissue, and wherein the laser beam delivery optical system includes a beam combiner configured to combine an OCT sample beam and the pulsed laser beam into a common optical path.

It is to be understood that both the foregoing general description and the following detailed description are exemplary and explanatory and are intended to provide further explanation of the invention as claimed.

DETAILED DESCRIPTION OF THE INVENTION

Figure 1:
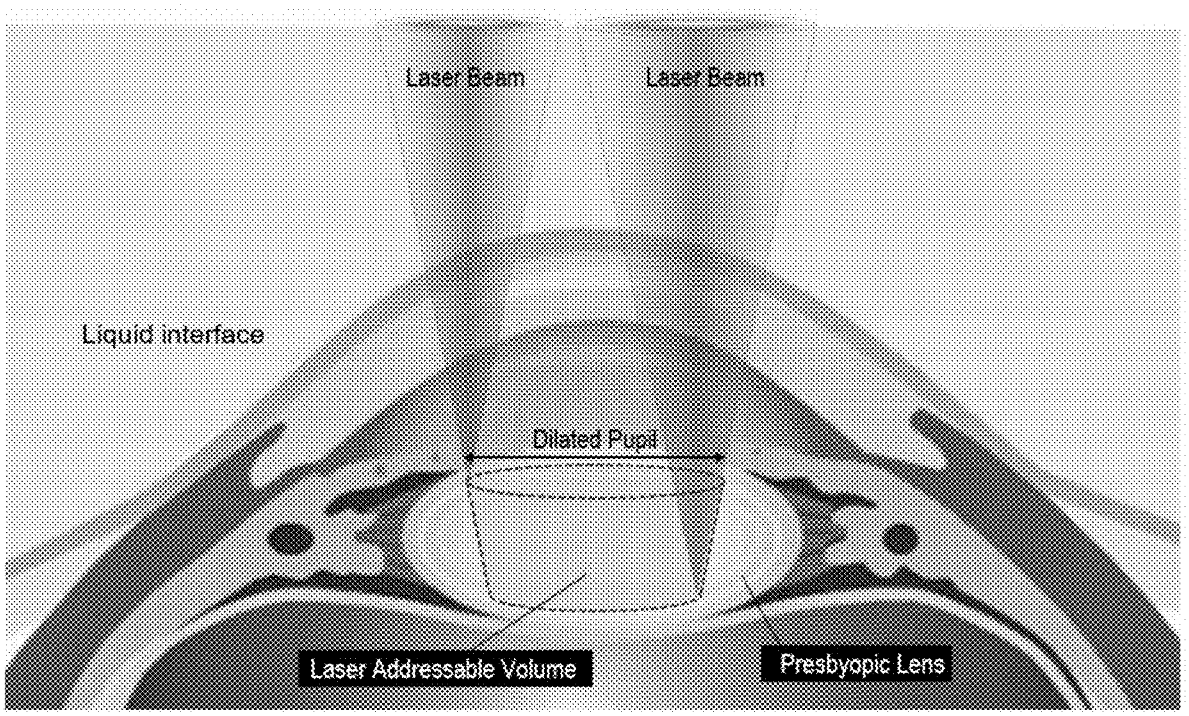
FIG. 1 is a schematic illustration of eye anatomy, laser beam, and treatment volume for laser presbyopia treatment.

As discussed earlier, treating presbyopia by delivering laser pulses into the crystalline lens to soften the lens so as to improve accommodation has been proposed. While many references describe laser systems intended for presbyopia treatment, they do not provide ranges of laser system parameters that would permit a clinical application of the proposed methods. The wide ranges of laser system parameter values described in many references reflect a fundamental lack of understanding of many key aspects of treating the crystalline lens with pulsed laser beams.

When delivering femtosecond laser pulses to treat the crystalline lens, the numerical aperture of the laser beam is limited by the pupil diameter of the eye (4-8 mm after dilation) to a low range of NA=0.125-0.20. The conventional laser pulse focal volume of such low NA beam is large, leading to large volume of tissue damage per pulse and severe light scattering in the treated lens tissue. According to embodiments of the present invention, lens softening for laser presbyopia treatment is practiced in a new parameter regime, referred to herein as the pulse-duration limited focal volume regime, which allows significant (e.g. 10 times) reduction in the laser pulse focal volume by adequately selecting the laser pulse duration for given NAs and laser wavelengths. This laser parameter regime allows the laser pulses to soften the lens while minimizing light scattering in the treated lens tissue. This is a fundamental principle for practical laser presbyopia treatment system designs.

Currently, none of the ophthalmic surgical lasers operates in the pulse-duration limited focal volume regime, including all femtosecond lasers for laser cataract surgery and laser refractive surgery on the market and the femtosecond and picosecond lasers used in the limited investigational studies for laser presbyopia treatment described earlier. Although there are patents describing laser presbyopia treatment via the laser induced optical breakdown mediated effects (see the patents mentioned in the Background section above), the lack of understanding of the fundamental principle is evident as seen from the proposed audaciously wide ranges of laser parameters in many of these references which contain ranges that will not work at all for various fundamental reasons. These prior patents do not teach the basic principles and requirements for the selection of laser parameters and the design of a laser presbyopia treatment system. The laser presbyopia treatment as described in these prior patents is far from being ready for practical application.

Embodiments of the present invention and the theories and considerations that support the design and operation of a laser system for presbyopia treatment are described in detail below.

Limitations on Numerical Aperture for Lens Treatment

Because both laser presbyopia treatment and laser cataract surgery must use a low NA (0.125-0.20) laser beam to treat the lens due to the limit of pupil diameter, the laser beam has a large conventional focal volume. Large focal volume is not an issue for laser cataract surgery, because the laser treated lens tissue will be removed out of the lens capsule completely, and an artificial intra-ocular-lens (IOL) will be implanted. For laser presbyopia treatment, however, the treated lens will continue to function, so the focal volume must be minimized to ensure minimum light scattering in the treated lens tissue.

FIG. 1 is a schematic illustration of eye anatomy, laser beam, and treatment volume for laser presbyopia treatment. In this example, the beam paths in the crystalline lens for laser presbyopia treatment are similar to that for laser cataract surgery. A liquid patient interface is used to couple the eye to the laser beam delivery optical system, where the cornea is not deformed or minimally deformed by the liquid. The liquid patient interface is advantageous over a hard contact patient interface because the latter can cause wrinkles on the posterior cornea to cause significant beam distortion for both laser treatment and for OCT (optical coherence tomography) imaging.

Figure 2:
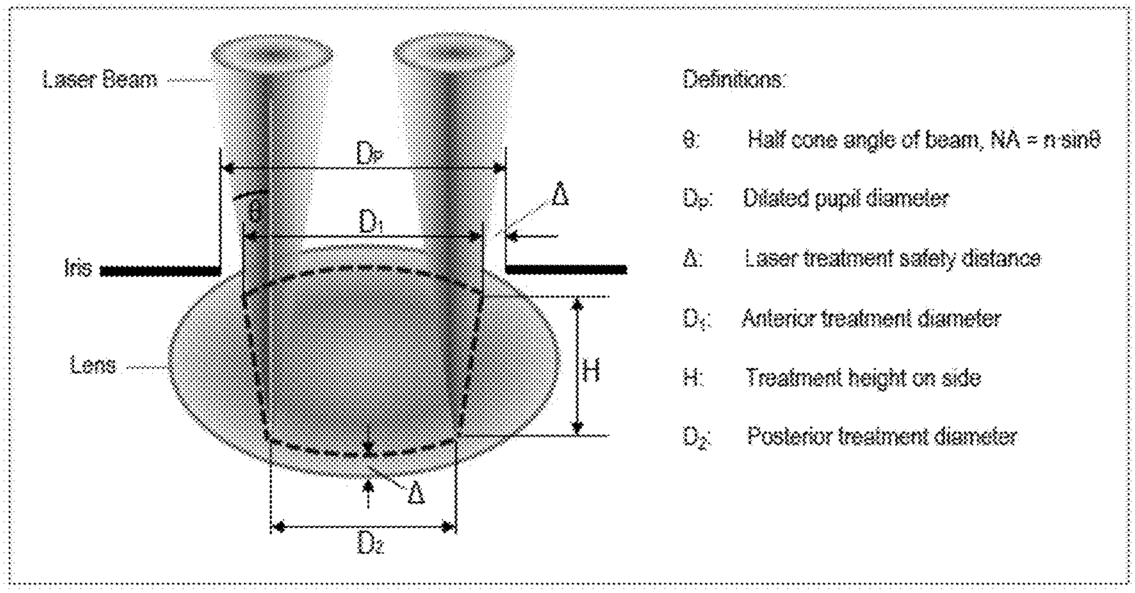
FIG. 2 shows a geometric model for calculating the posterior and anterior diameters of the treatment volume in the crystalline lens in relation to pupil size and numerical aperture of the laser beam.

A major constraint of the system is due to the limited pupil diameter of the eye, which is typically 4-8 mm after dilation. FIG. 2 illustrates a geometric model showing the relation between pupil diameter, numerical aperture of the pulsed laser beam, and treatment volume (the volume that can be reached by the laser beam) within the crystalline lens. Table I below shows the calculated posterior treatment diameter $D_2$ for a typical dilated pupil diameter of 7 mm for NA in the range of 0.125-0.30. Other parameters used in the calculation are: Refractive index of the lens: n=1.42; Treatment safety distance: Δ=5 mm; Anterior treatment diameter: $D_1$=6.0 mm; Treatment side height: H=3.5 mm. Table I also shows the half cone angle of the laser beam θ.

TABLE I

Numerical aperture and posterior treatment diameter in the lens

| NA | 0.125 | 0.150 | 0.175 | 0.200 | 0.225 | 0.250 | 0.275 | 0.300 |
|---|---|---|---|---|---|---|---|---|
| θ (°) | 5.1 | 6.1 | 7.1 | 8.1 | 9.1 | 10.1 | 11.2 | 12.2 |
| $D_2$ (mm) | 5.4 | 5.3 | 5.1 | 5.0 | 4.9 | 4.7 | 4.6 | 4.5 |

As seen from Table I, a posterior treatment diameter of about 5.4 mm to 4.5 mm corresponds to an NA range of 0.125-0.30. The choice of NA for the laser presbyopia treatment requires various tradeoffs. The lower the NA, the larger the focus spot size and focal volume of the laser beam, hence the higher the required pulse energy in order to achieve desired laser power density. The higher the NA, the smaller the treatment volume. Too high an NA also tends to induce significant aberration to the laser beam resulting in deteriorated focal quality, the latter also results in higher required pulse energy in order to achieve desired laser power density.

Figure 3:
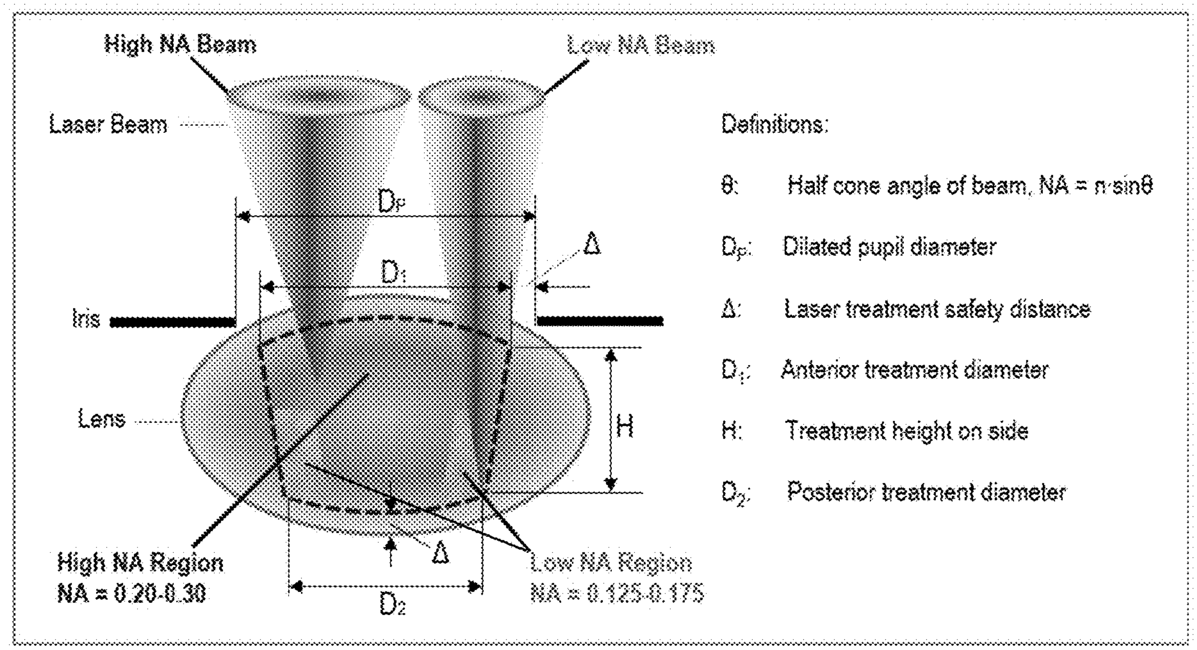
FIG. 3 schematically illustrates a method of treating the crystalline lens using laser beams having different numerical apertures.
Figure 4:
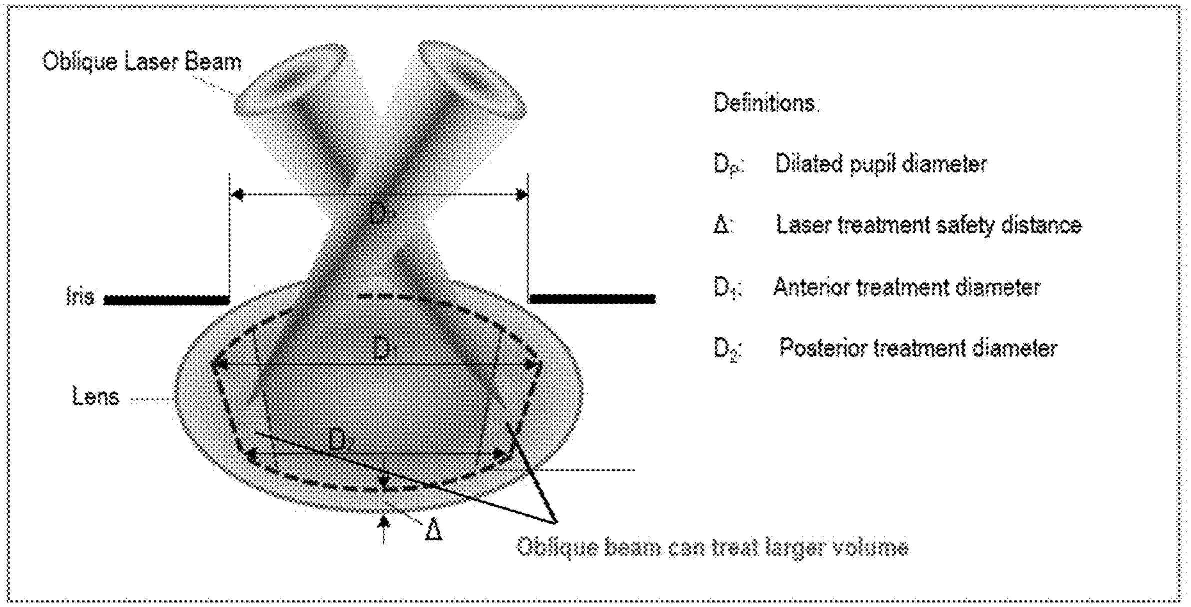
FIG. 4 schematically illustrates a method of treating the crystalline lens using laser beams having oblique incident angles.

An optimum way to select the NA for laser presbyopia treatment is to use a higher NA (e.g., 0.2-0.3) beam to treat the anterior and center portions of the lens, and use a lower NA (e.g., 0.125-0.175) beam to treat the posterior and peripheral portions, as shown in FIG. 3. Another way to increase the treatment volume in the lens is to use an oblique incident laser beam, as shown in FIG. 4. The oblique incident beam can treat an extra portion of the lens located around the volume reached by the normal incident beam in the example shown in FIG. 2.

NA Limited Focal Volume and Pulse-Duration Limited Focal Volume

It is known that a femtosecond laser pulse interacts with the tissue through plasma formation when the peak power density (power per unit volume) is above the laser-induced optical breakdown threshold (referred to as the plasma threshold), which is on the order of $10^{13}$ W/cm$^3$ for water and transparent eye tissues. In the plasma region, the tissue will be vaporized due to the high temperature of the plasma; in the vicinity of the plasma, the tissue will be cut or separated mechanically by the plasma-induced cavitation bubble and shockwave. The volume of the plasma is approximately determined by the focal volume around the focal point where the photons are highly concentrated. The focal volume is the volume encircled by the ellipsoid where the photon density at the boundary is half that in the center of the focal volume. For example, if the pulse energy is twice the threshold pulse energy, the whole focal volume is above the plasma threshold—the plasma volume is approximately equal to the focal volume. Since the pulse energy can be adjusted, the focal volume is the figure of merit for the magnitude of laser-tissue interaction in system design for laser presbyopia treatment. To achieve minimum light scattering for laser presbyopia treatment, the smaller the focal volume, the better.

Figure 5:
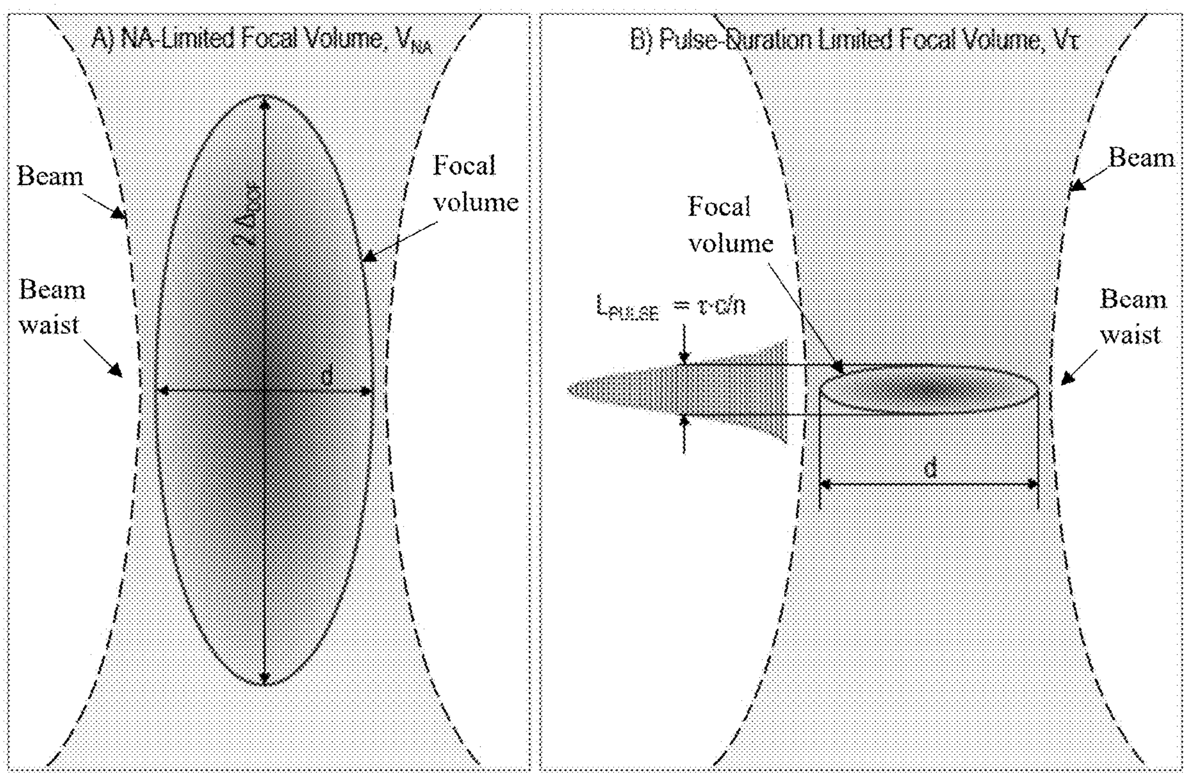
FIG. 5 schematically illustrates a comparison of the NA limited focal volume, $V_{NA}$, and the pulse-duration limited focal volume, $V_{\tau}$, according embodiments of the present invention.

In conventional laser system designs, including all femtosecond lasers for laser refractive surgery and laser cataract surgery on the market, the focal volume is solely determined by the laser wavelength and the NA of the beam. Since the wavelengths of most of these lasers are about 1 μm (1.030-1.053 μm), such focal volume may be referred to as "NA limited focal volume", $V_{NA}$, as shown in FIG. 5, diagram A on the left. However, because NA is limited by the geometric constraints of the eye as discussed earlier, there is little room to select the value of $V_{NA}$ for laser presbyopia treatment.

According to embodiments of the present invention, to achieve minimum light scattering in the treated lens tissue for laser presbyopia treatment, the focal volume should be limited by the laser pulse duration, referred to as the "pulse-duration limited focal volume", $V_\tau$, as shown in FIG. 5, diagram B on the right. The pulse duration of the laser beam is then selected based on the requirement for $V_\tau$.

In both diagrams in FIG. 5, the dashed-line curves schematically represent the shape of the laser beam near the beam focus. The narrowest point of the beam is referred to as the beam waist. The focal volume is indicated by the ellipsoid. In both cases ($V_{NA}$ and $V_\tau$), the volume of the ellipsoid is given by the standard formula $(4\pi/3)\cdot a^2\cdot b$, where a is the FWHM radius at the focal plane, and b is a half of the FWHM axial length of the ellipsoid. The focal volumes $V_{NA}$ and $V_\tau$ may be calculated as follows.

The FWHM focus diameter d (unit: μm) of the laser pulse is:

$$d \approx 0.58\,\lambda/NA \tag{1}$$

where λ is the wavelength of the laser beam in air (unit: μm), which is a laser system parameter, and NA is the numerical aperture, which is a design parameter of the beam delivery optics and a constant throughout the beam path. NA is related to the half cone angle of the laser beam delivered in the crystalline lens, θ, by NA=n·sin θ, where n is the refractive index of the lens (n=1.42). Equation (1) is an empirical approximation that is accurate for many known ophthalmic laser systems.

The depth of focus (half) in the lens, $\Delta_{DOF}$ (unit: μm), is given by:

$$\Delta_{DOF} \approx 0.764\; n\cdot\lambda/NA^2 \tag{2}$$

This equation is derived as follows. For a Gaussian beam, which is a good approximation for a laser beam, $\Delta_{DOF}=n\pi w_0^2/\lambda$, where $w_0$ is the $1/e^2$ radius at the focus, and $w_0\approx 0.85$ d. Using the relation between d and NA (Equation (1)), Equation (2) is obtained. $2\Delta_{DOF}$ is the FWHM axial length of the beam at the focus.

For a continuous laser beam or for a long pulse duration (i.e., the spatial pulse length is greater than the depth of focus), the focal volume is the volume of the ellipsoid defined by d and $\Delta_{DOF}$. Thus, the NA limited focal volume, $V_{NA}$ (unit: $\mu m^3$), is given by:

$$V_{NA}=(\pi/3)\cdot d^2\cdot\Delta_{DOF}\approx 0.269\ n\cdot\lambda^3/NA^4 \tag{3}$$

I.e., the focal volume is determined by NA when n and λ are given. Table II below shows the estimated values of $V_{NA}$ for a number of NAs within the applicable range for laser presbyopia treatment, for two exemplary laser wavelengths.

TABLE II(A)

| NA-limited focal volume for $\lambda$ = 1.03 μm | | | | | | | | |
|---|---|---|---|---|---|---|---|---|
| NA | 0.125 | 0.150 | 0.175 | 0.200 | 0.225 | 0.250 | 0.275 | 0.300 |
| d (μm) | 4.8 | 4.0 | 3.4 | 3.0 | 2.7 | 2.4 | 2.2 | 2.0 |
| $\Delta_{DOF}$ (μm) | 71.5 | 49.7 | 36.5 | 27.9 | 22.1 | 17.9 | 14.8 | 12.4 |
| $V_{NA}$ ($\mu m^3$) | 1711 | 825 | 445 | 261 | 163 | 107 | 73 | 52 |

TABLE II(B)

| NA-limited focal volume for $\lambda$ = 0.75 μm | | | | | | | | |
|---|---|---|---|---|---|---|---|---|
| NA | 0.125 | 0.150 | 0.175 | 0.200 | 0.225 | 0.250 | 0.275 | 0.300 |
| d (μm) | 3.5 | 2.9 | 2.5 | 2.2 | 1.9 | 1.7 | 1.6 | 1.5 |
| $\Delta_{DOF}$ (μm) | 52.1 | 36.2 | 26.6 | 20.3 | 16.1 | 13.0 | 10.8 | 9.0 |
| $V_{NA}$ ($\mu m^3$) | 660 | 318 | 172 | 101 | 63 | 41 | 28 | 20 |

By way of example, one laser system for laser cataract surgery uses NA=0.175, where the NA limited focal volume is $V_{NA}$~ 445 $\mu m^3$, and the measured LIOB pulse energy threshold is about 0.8 μJ (as delivered in the tissue). Note that the LIOB pulse energy threshold is dependent on the focal spot size which is in turn dependent on laser wavelength, and the above example is given for a λ=1.03 μm laser. For laser presbyopia treatment, it is desirable to limit the focal volume to 50 $\mu m^3$ or less, so the corresponding LIOB pulse energy threshold is about 0.09 μJ (=90 nJ) or less. Based on their experience with laser cataract surgery systems, the inventors learned that in such an energy range, the laser pulses can cut cornea tissue while inducing minimum light scattering in the treated tissue. Under the reasonable assumption that the lens tissue will respond to laser pulses in a similar manner as the cornea tissue, the inventors propose to use this pulse energy range to perform laser presbyopia treatment. From Table II(A), it can be seen that for λ=1.03 μm, a focal volume of 50 $\mu m^3$ or less cannot be achieved by a NA limited focal volume; i.e., laser presbyopia treatment under such a requirement should use a pulse-duration limited focal volume.

As seen in FIG. 5, under the NA limited regime, the focal volume fills the entire length of beam waist region (the laser pulse is longer than the depth of focus), while under the pulse-duration limited regime, the axial length of the focal volume is limited by the spatial length of the laser pulse which is shorter than the depth of focus. Thus, when the spatial pulse length, $L_{PULSE}$, is shorter than $2\Delta_{DOF}$, the pulse-duration limited focal volume of the ellipsoid, $V_\tau$ (unit: $\mu m^3$), is given by:

$$V_\tau=(4\pi/3)(d/2)^2\cdot(L_{PULSE}/2)\approx 0.176\lambda^2\cdot L_{PULSE}/NA^2, \tag{4}$$

Using pulse duration τ, this means $$V\tau\approx 0.176\ c\cdot\tau\cdot\lambda^2/(n\cdot NA^2)\text{ if }\tau<1.53\ n^2\cdot\lambda/(c\cdot NA^2) \tag{5}$$

where $L_{PULSE}$ (unit: μm) is the FWHM spatial pulse length of the laser pulses in the crystalline lens, c (unit: μm/fs) is the speed of light in air, and τ (unit: fs) is the FWHM pulse duration of the laser pulses. $L_{PULSE}$ is related to τ by: $L_{PULSE}=\tau\cdot c/n$. The FWHM pulse duration τ may be set by the laser system.

Let $V_{max}$ be the maximum focal volume allowed for laser presbyopia treatment, and $\tau_{max}$ the maximum pulse duration that gives the maximum focal volume, the following will be required for laser presbyopia treatment:

$$\tau\le\tau_{max}=\frac{5.682\ n\cdot NA^2\cdot V_{max}}{c\cdot\lambda^2} \tag{6}$$

I.e., the pulse duration is required to be below a maximum value $\tau_{max}$.

From Table II(A), it can be seen that, for λ=1.03 μm and $V_{max}$=50 $\mu m^3$, the pulse duration for laser presbyopia treatment must satisfy Equation (6) for NA≤0.30; for λ=0.75 μm, Equation (6) must be met for NA≤0.225; for NA≥0.25, the NA-limited focal volume is already smaller than 50 $\mu m^3$, so the pulse duration can be longer than the value given by Equation (6) (i.e., the focal volume does not need to be pulse-duration limited).

Figure 6:
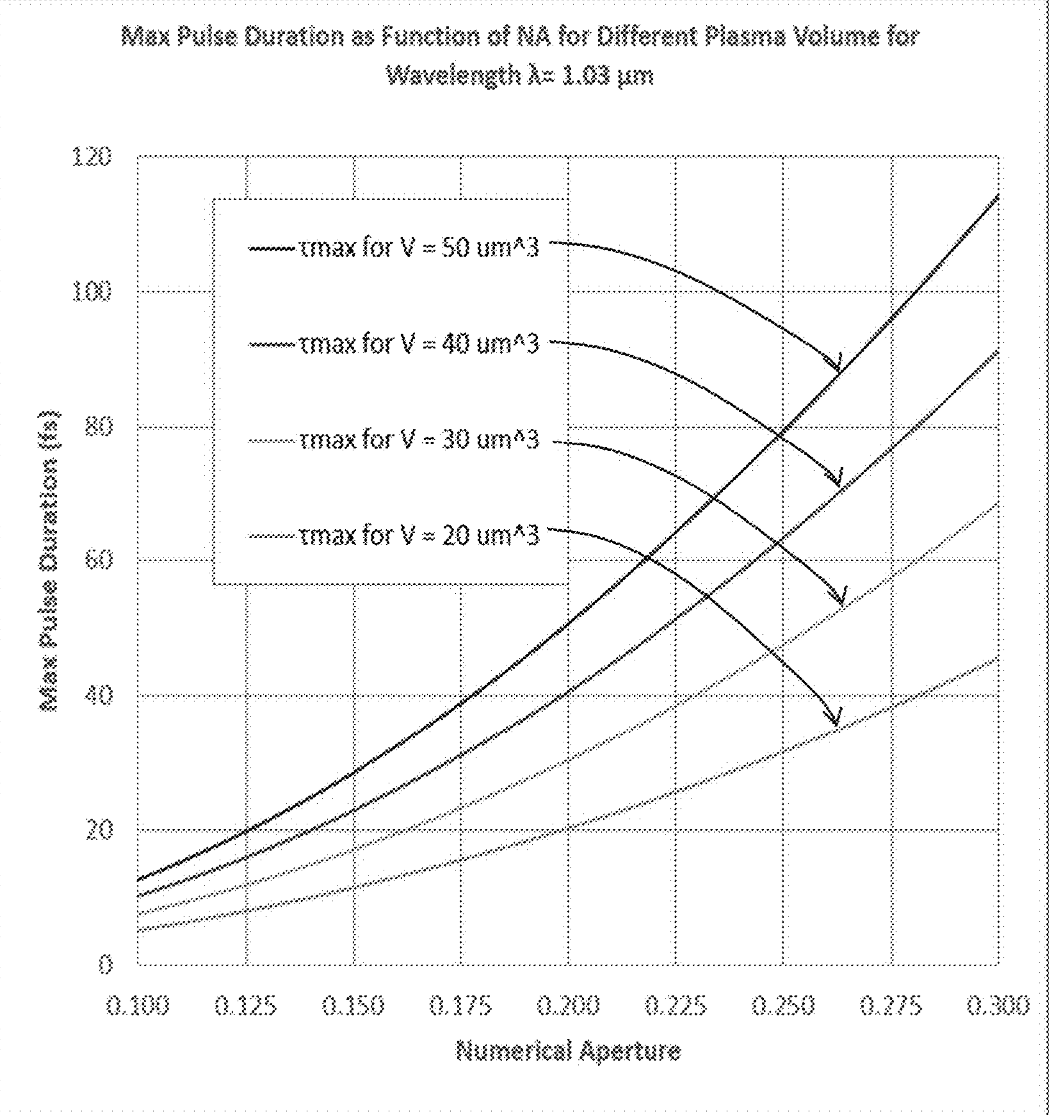
FIG. 6 illustrates the maximum pulse duration as a function of NA for different maximum focal volumes according to embodiments of the present invention.

FIG. 6 illustrates the maximum pulse duration $\tau_{max}$ as a function of NA for different maximum focal volumes $V_{max}$ from 50 $\mu m^3$ to 20 $\mu m^3$, for λ=1.03 μm. For $V_{max}$=50 $\mu m^3$, for example, the maximum pulse duration $\tau_{max}$ ranges from 13 to 114 fs for the NA range of 0.100-0.300. For the practical NA range of 0.125-0.200 (for treating at least the posterior and peripheral regions of the lens), the maximum pulse duration $\tau_{max}$ ranges from 19 to 51 fs for $V_{max}$=50 $\mu m^3$, or from 8 to 20 fs for $V_{max}$=20 $\mu m^3$. The table in FIG. 6 gives exemplary values of $V_{max}$ between 50 $\mu m^3$ and 20 $\mu m^3$. The $V_{max}$ value 50 $\mu m^3$ corresponds to a photodisruption energy threshold of about 90 nJ, which is sufficiently low based on experiences of femtosecond laser application on cornea and there is minimum tissue damage and light scattering. Usually, the pulse energy used in treatment should be at least 30% above the threshold to ensure that the laser pulse energy is always above the photodisruption threshold given possible tolerances. The $V_{max}$ value 20 $\mu m^3$ is at the low end of practically achievable results. For NA=0.125, $V_{max}$=20 $\mu m^3$ corresponds to a pulse duration of about 8 fs, which requires a theoretical laser wavelength spectral bandwidth of 197 nm, and practical bandwidth of about 600 nm. For spectral widths wider than a such width, the GVD pre-compensation will have non-linear terms and also the laser will have wavelength components that overlap with the OCT wavelength, which presents significant technical challenges.

Exemplary Laser Beam Parameters for Presbyopia Treatment

An example of how to choose laser beam parameters for a particular laser system is described below. As discussed earlier, the pulse energy threshold for inducing laser-induced optical breakdown is determined by the focal volume. In one example, for a $\lambda$=1.03 μm laser, when the focal volume is limited to 50 $\mu m^3$ (by employing a pulse duration calculated from Equation (6) or the table in FIG. 6), the LIOB pulse energy threshold is about 90 nJ. Using this example, when the focal volume is limited to 20 $\mu m^3$, the LIOB pulse energy threshold is about 36 nJ. Using these empirical values and Equation (6), the relationship between the LIOB pulse energy threshold $E_0$ (unit: nJ) and the corresponding maximum pulse duration $\tau_{max}$ may be expressed as:

$$\tau_{max} = 3.157 n \cdot NA^2 \cdot E_0 / (c \cdot \lambda^2) \quad (7)$$

where, $\tau_{max}$ is in fs, the photodisruption threshold energy is in nJ, the wavelength is in μm, and the speed of light c=0.3 μm/fs.

In other words, under the pulse-duration limited regime, if the pulse energy is chosen to be a particular value E, then the pulse duration $\tau$ should be shorter than the value calculated from Equation (7) in order to limit the focal volume such that the energy density in the lens tissue reaches the LIOB threshold, i.e.:

$$\tau \leq 3.157\ n \cdot NA^2 \cdot E_0 / (c \cdot \lambda^2) \quad (8)$$

In practice, the pulse duration may be chosen to be larger than, for example, a half of the value calculated from Equation (8).

Conversely, if the pulse duration is chosen to be a particular value $\tau$, then the pulse energy E should be greater than the value calculated from Equation (7) in order to ensure that the energy density in the lens tissue reaches the LIOB threshold, i.e.:

$$E_0 \geq \tau \cdot c \cdot \lambda^2 / (3.157\ n \cdot NA^2) \quad (9)$$

In practice, the treatment pulse energy may be chosen to be 1.3 to 2.0 times the photodisruption threshold energy $E_0$ as given in Equation (9). Lower than $1.3 \times E_0$ may cause black spots, i.e., uncut locations; higher than $2 \times E_0$ can increase light scattering.

Of course, the choices of pulse energy and pulse duration should be such that the operation is under the pulse-duration limited regime (Equation (5)).

Note that the above example described in Equations (7)-(9) is for a particular laser system; for different laser systems, various empirical values such as the LIOB pulse energy threshold will be different and can be measured, but the principles described above still apply.

To summarize, the laser presbyopia treatment according to embodiments of the present invention employs low pulse energy and short pulse duration such that the laser pulses produce laser-induced optical breakdown in the lens tissue within a focal volume that is limited by pulse duration. Preferably, for a $\lambda$=1.03 μm laser beam, the pulse energy ranges from 1 nJ to 500 nJ per pulse, and the pulse durations ranges from 1 fs to 200 fs. Practically, the photodisruption threshold pulse energy is 36 nJ to 90 nJ and the pulse duration is 8 fs to 51 fs (the lower end of the pulse energy and pulse duration ranges corresponds to NA=0.125 and $V_\tau$=20 $\mu m^3$; the upper end of the ranges corresponds to NA=0.200 and $V_\tau$=50 $\mu m^3$). The pulse energy and pulse duration satisfy Equations (8) and (9).

Laser System

Figure 7:
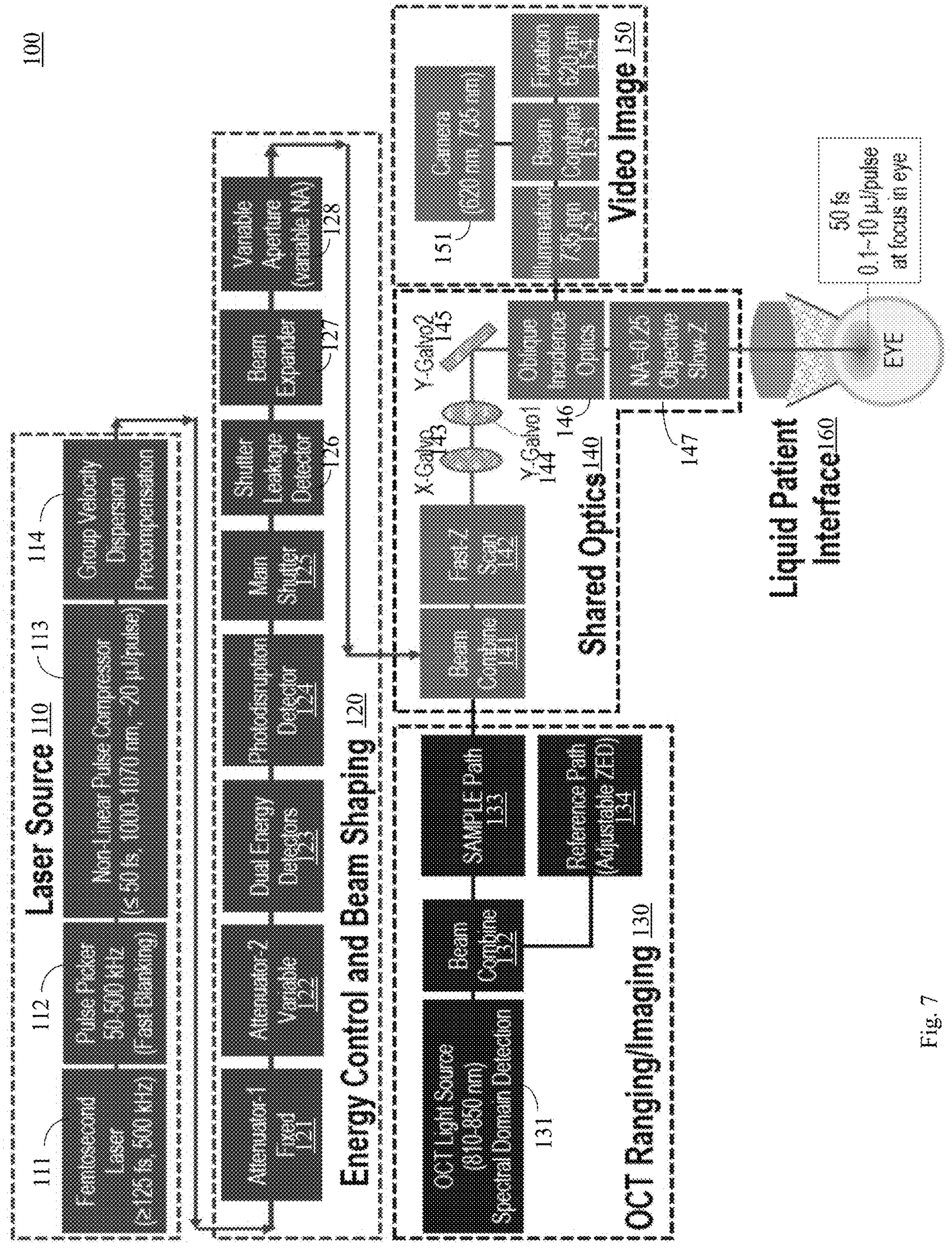
FIG. 7 is a schematic diagram of an exemplary ophthalmic laser surgery system that may be employed to implement laser presbyopia treatment according to embodiments of the present invention.

FIG. 7 is a schematic diagram of an exemplary ophthalmic laser surgery system that may be employed to implement laser presbyopia treatment according to embodiments of the present invention. The laser system 100 includes a laser source 110, an energy control and beam shaping sub-system 120, an OCT ranging and imaging sub-system 130, a share optical sub-system 140, and a video imaging sub-system 150. The system also includes a controller (not shown in FIG. 7), such as a computer or a processor with a memory storing data and control programs, which is coupled to and controls the various other components and sub-systems of the laser surgery system. The energy control and beam shaping sub-system 120 and the share optical sub-system 140 may be collectively referred to as the laser beam delivery optical system.

In a preferred embodiment, the laser source 110 includes a femtosecond laser source 111 that generates a pulsed laser beam, a pulse picker 112 that performs fast-blanking of the pulses, a non-linear pulse compressor 113 that compresses the pulse duration, and a group velocity dispersion pre-compensation device 114. In an exemplary laser source, the pulsed laser beam generated by the femtosecond laser 111 has a wavelength of 1030 nm, a pulse duration greater than 125 fs, and pulse repetition rate of about 500 kHz; the pulse picker reduces the pulse repetition rate to 50-500 kHz; the non-linear pulse compressor 113 compressed the laser pulses to shorter than 200 fs, preferably, shorter than 100 fs, and more preferably, shorter than 50 fs. In the illustrated example, the pulsed laser beam output from the non-linear pulse compressor 113 has a wavelength range of 1000-1070 nm, pulse duration of less than 50 fs, and pulse energy of about 20 μJ per pulse.

Other technologies may be used to generate the ultra-short pulsed laser beam for presbyopia correction. For example, an optical parametric modulation (OPM) or optical parametric amplifier (OPA) with input pulses from a separate femtosecond laser may be used to generate a beam with shorter than 100 fs pulses at a different wavelength (from the original femtosecond pulses). Alternatively, a femtosecond laser oscillator or chirped-pulse-amplification may be used to generate a beam with shorter than 100 fs pulses. Further, in lieu of a pulse picker, other suitable means may be used to perform fast-blanking to allow fast and versatile laser scanning pattern control for presbyopia correction.

More generally, the laser source 110 may be any suitable laser source that is capable of generating a pulsed laser beam having a wavelength of 0.80 μm to 1.1 μm, a pulse duration of 10 fs to 200 fs, a pulse repetition rate of 100 kHz to 2 MHz, and a pulse energy of 0.2 μJ to 50 μJ.

Figure 8:
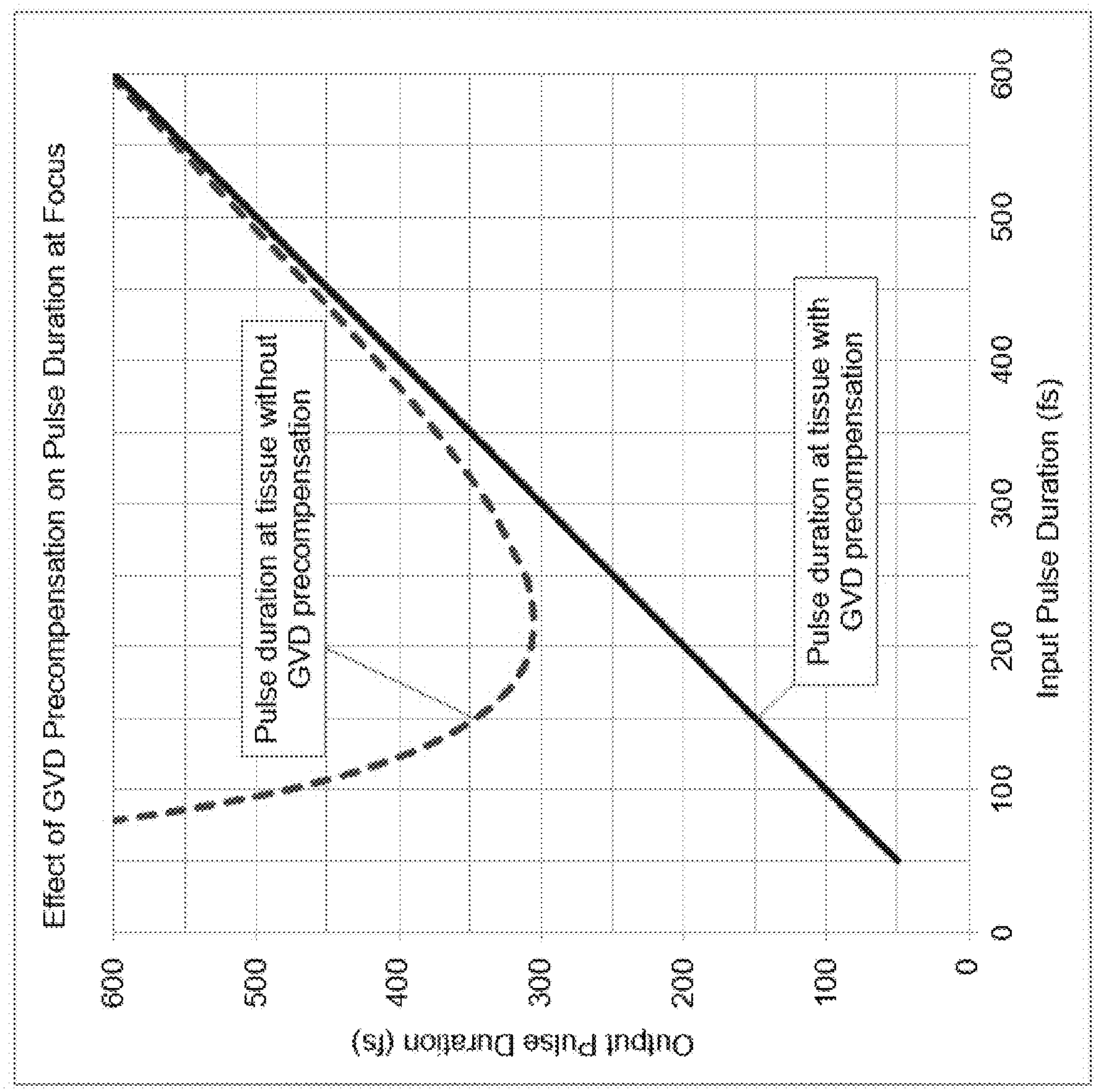
FIG. 8 shows the effect of group velocity dispersion pre-compensation on pulse duration at the beam focus according to embodiments of the present invention.

The group velocity dispersion pre-compensation device 114 is an important component of the ophthalmic laser surgery system for laser presbyopia treatment. It should be emphasized that the temporal pulse duration and spatial pulse length discussed earlier are for laser pulses as delivered into the crystalline lens tissue. For very short pulse durations, group velocity dispersion (GVD) induced pulse broadening effect in the beam delivery optical system causes significant broadening of the pulse duration. FIG. 8 shows the relationship between the input pulse duration (e.g., the pulse duration of the original laser beam produced by the non-linear pulse compressor 113) and the output pulse duration after passing through an exemplary laser beam delivery optical system, with and without GVD pre-compensation. As seen in FIG. 8, in this example, the input pulse duration of 50 fs will be lengthened to above 600 fs due to group velocity dispersion without pre-compensation. Generally speaking, GVD pre-compensation is desired for pulse duration shorter than about 300 fs. Such pre-compensation can ensure that the pulse duration at the output end of the optical system remains approximately the same as that generated by the non-linear pulse-compressor 113. With GVD pre-compensation, the shortest pulse duration that the laser source can possibly provide (also called band-width limited pulse duration) can be achieved at the tissue. The group velocity dispersion pre-compensation device 114 may employ any suitable technology, such as adjustable optical grating components.

In the preferred embodiment, the energy control and beam shaping sub-system 120 includes a two-stage polarization attenuator (described in more detail later), an energy detector 123 for measuring the pulse energy (e.g., a dual energy detector including a beamsplitter that directs portions of the incoming laser beam to two photodiodes), a photodisruption detector 124 for measuring a returned portion of the laser beam which is reflected by the target tissue and collected by the laser beam delivery optics (e.g., a beamsplitter that directs a portion of the returned laser beam to a third photodiode or an image sensor), a main laser shutter 125, a shutter leakage detector 126 downstream of the shutter (e.g., a beamsplitter which directs a portion of the incoming laser beam to a fourth photodiode), a beam expander 127 for changing the size of the laser beam, and a variable aperture 128.

The two-stage attenuator includes a first, fixed attenuator 121 and a second, variable attenuator 122. In a preferred embodiment, each attenuator includes a rotatable half-wave plate and a polarization beamsplitter. Two-stage attenuation is advantageous in the system for laser presbyopia treatment because of the extremely short laser pulse duration and the low pulse energy. Due to the extremely short pulse duration, the laser pulses have a relatively wide wavelength spectral width, which will affect the performance of polarization attenuators. The wavelength spectral width (FWHM), $\Delta\lambda$, is inversely proportional to the pulse duration. In theory, it is given by:

$$\Delta\lambda = \frac{2(\ln 2)\cdot\lambda^2}{\pi c\cdot\tau}$$

For example, for $\lambda$=1.03 μm and $\tau$=50 fs, the theoretical $\Delta\lambda \approx 31.5$ nm (FWHM) (for comparison, for an exemplary laser system for laser cataract surgery, $\tau \approx 400$ fs, the theoretical $\Delta\lambda \approx 3.9$ nm). In practice, the measured full range of spectral width often covers 980-1080 nm with a center wavelength at about 1.03 μm. Such a wide spectrum will affect the performance of the polarization attenuator because the rotatable half-wave plate used in the attenuator provides exact half-wave phase shift only for one specific wavelength; for other wavelengths, the phase shift will not be an exact half-wave, the original linear polarization of the laser will become elliptically polarized after passing the half-wave plate, and some part of the beam will leak through the attenuator even at the extinction point, leading to a relatively high non-zero extinction leakage. Therefore, it is favorable to use a 2-stage polarization attenuator (i.e., two attenuators in series) to ensure energy control for the entire pulse energy range.

Two-stage attenuation is particularly necessary when the output pulse energy is at the low end of the total energy range of the laser source. For example, the pulse compressor requires a high input pulse energy (about 40 μJ/pulse) and therefore gives high output pulse energy after pulse compression, but the laser presbyopia treatment requires low pulse energy (e.g., about 0.3 μJ/pulse or lower). Using a two-stage attenuator can avoid operating the variable attenuator at the unstable extinction point. For example, using two attenuators each operating at 10% transmission (total transmission 1%) will be much more controllable than using one attenuator setting at 1% transmission. In a particular example, the first attenuator has a fixed transmission rate of about 10%, and the second attenuator has a variation transmission rate and is used to adjust the output laser pulse energy. In alternative embodiments, both attenuators may be variable attenuators.

The energy control and beam shaping subsystem 120 uses a variable aperture 128 to adjust the numerical aperture of the laser beam during the laser procedure, to access the crystalline lens and to treat maximum volumes in the lens without changing the focus position (see FIGS. 1-3). Any suitable structure may be used to implement the variable aperture, such as an iris.

The photodisruption detector 124 may be used to monitor the laser pulse interaction with the crystalline lens tissue for real-time control of pulse energy and cut pattern.

The OCT ranging and imaging sub-system 130 includes an OCT light source and spectral domain detector 131, a beam combiner 132, a sample beam path 133 and a reference beam path 134. Preferably, a polarization-sensitive OCT is used. The OCT sub-system is used to map lens tissue and fiber distribution (e.g., via birefringence, diattenuation, depolarization) to assist presbyopia treatment planning and post-treatment measurement. The structure and operation of the OCT sub-system are generally known and further details are omitted here. Other suitable devices may be used to perform ranging and imaging functions.

The shared optical sub-system 140 includes a beam combiner 141 that combines the OCT sample beam and the treatment laser beam generated by the energy control and beam shaping sub-system 120 into a common optical path. An X, Y and Z scanning system, such as a fast-Z scanner 142, an X galvo mirror 143 and two Y galvo mirrors 144 and 145, scans the treatment laser beam in the target tissue in desired treatment patterns. The shared optical system 140 also includes optics 146 to combine the light beams of the illumination source 152, the video camera 151, and the fixation light source 154 of the video imaging sub-system 150 into the shared optical path. Then, an objective lens 147 with a slow-Z scanning capability focuses the treatment laser beam to the target eye tissue. The illumination source and the video camera provide video images for the eye during the procedure. The fixation light source provides a light target for aligning the patient's visual axis with the system's optical axis.

The optics 146 preferably also includes optics (e.g., focusing lenses) that facilitate oblique incidence of the laser beam into the crystalline lens (see FIG. 4). This is realized by using an entocentric lens which is a compound lens with its entrance or exit pupil located inside the lens. The exit beam from the entocentric lens is oblique, depending on the angle of the incidence. Using oblique optical beam design helps to minimize the pupil shadow effect to achieve the largest possible treatment volume. This is critical to achieve up to 4D gain in accommodation.

The ophthalmic laser surgery system described above may also be used to perform other procedures, such as corneal and lens incisions in laser cataract surgeries, by operating the laser system using different parameters. For lens fragmentation, for example, the pulse energy may be up to 10 μJ. For corneal incisions, such as penetrating clear corneal incisions and arcuate incisions, for example, about 0.2 μJ pulse energy may be used, which may result in smoother cutting quality and faster healing than using conventional laser systems.

It will be apparent to those skilled in the art that various modification and variations can be made in the laser presbyopia treatment method and related apparatus of the present invention without departing from the spirit or scope of the invention. Thus, it is intended that the present invention cover modifications and variations that come within the scope of the appended claims and their equivalents.

The invention claimed is:

1. A laser treatment method for treating presbyopia of a crystalline lens of a patient's eye, comprising:

generating a pulsed laser beam comprising a plurality of laser pulses;

focusing the pulsed laser beam to a beam focus inside the lens, wherein a numerical aperture NA of the laser beam is between 0.125 and 0.20, and a focal volume of the beam focus within the lens is less than 50 μm$^3$, wherein the focal volume is defined by a diameter of the beam focus at a focal plane and a spatial pulse length of the laser pulses in the lens; and scanning the pulsed laser beam in the lens according to a treatment pattern, to induce optical breakdown of lens tissue at the beam focus to reduce Young's modulus of the tissue.

2. The laser treatment method of claim 1, wherein the focal volume of the beam focus within the lens is greater than 20 μm$^3$.

3. The laser treatment method of claim 1, wherein generating the pulsed laser beam includes generating an original pulsed laser beam and performing group velocity dispersion pre-compensation of the original pulsed laser beam.

4. The laser treatment method of claim 1, wherein when scanning the pulsed laser beam in the lens according to a treatment pattern, the pulsed laser beam has a first numerical aperture when treating an anterior and center portion of the lens, and has a second numerical aperture which is lower than the first numerical aperture when treating a posterior and peripheral portion of the lens.

5. The laser treatment method of claim 1, wherein scanning the pulsed laser beam in the lens according to a treatment pattern includes scanning the pulsed laser beam at oblique incidence angles in the lens.

6. The laser treatment method of claim 1, wherein the pulsed laser beam focused inside the lens has a pulse duration of 8 fs to 51 fs and has a photodisruption threshold pulse energy of 36 nJ to 90 nJ.

7. The laser treatment method of claim 6, wherein generating the pulsed laser beam includes generating an original pulsed laser beam having an original pulse energy above 20 μJ, and attenuating the original pulsed laser beam using a two-stage polarization attenuator.

8. A laser treatment method for treating presbyopia of a crystalline lens of a patient's eye, comprising:

generating a pulsed laser beam comprising a plurality of laser pulses;

focusing the pulsed laser beam into a beam focus inside the lens, wherein a numerical aperture NA of the laser beam is between 0.125 and 0.2, a pulse duration r of the laser pulses in the lens is from 8 fs to 51 fs, and a photodisruption threshold pulse energy $E_0$ in the lens is from 36 nJ to 90 nJ; and scanning the pulsed laser beam in the lens according to a treatment pattern, to cause laser-induced optical breakdown of lens tissue at the beam focus to reduce Young's modulus of the tissue.

9. The laser treatment method of claim 8, wherein the pulse duration r and the photodisruption threshold pulse energy $E_0$ satisfy the relationship:

$$\tau \leq 3.157\ n \cdot NA^2 \cdot E_0 / (c \cdot \lambda^2)$$

where n is a refractive index of the tissue, c is the speed of light (c=0.3 μm/fs), and A (in μm) is a wavelength of the pulsed laser beam.

10. The laser treatment method of claim 8, wherein generating the pulsed laser beam includes generating an original pulsed laser beam having a pulse duration of less than 200 fs, and performing group velocity dispersion pre-compensation for the original pulsed laser beam so that the pulsed laser beam focused to the lens has a pulse duration of less than 200 fs.

11. The laser treatment method of claim 8, wherein when scanning the pulsed laser beam in the lens according to a treatment pattern, the pulsed laser beam has a first numerical aperture when treating an anterior and center portion of the lens, and has a second numerical aperture which is lower than the first numerical aperture when treating a posterior and peripheral portion of the lens.

12. The laser treatment method of claim 8, wherein scanning the pulsed laser beam in the lens according to a treatment pattern includes scanning the pulsed laser beam at oblique incidence angles in the lens.

13. The laser treatment method of claim 8, wherein generating the pulsed laser beam includes generating an original pulsed laser beam having an original pulse energy above 20 μJ, and attenuating the original pulsed laser beam using a two-stage polarization attenuator.

14. An ophthalmic laser surgery system for treating presbyopia of a crystalline lens of a patient's eye, the system comprising:

a laser source configured to generate a pulsed laser beam comprising a plurality of laser pulses; and a laser beam delivery optical system configured to focus the pulsed laser beam into a beam focus inside the lens and to scan the pulsed laser beam in the lens according to a treatment pattern, wherein a numerical aperture NA of the laser beam is between 0.125 and 0.2, and a focal volume of the beam focus within the lens is less than 50 μm$^3$, wherein the focal volume is defined by a diameter of the beam focus at a focal plane and a spatial pulse length of the laser pulses in the lens, and wherein the pulsed laser beam induces optical breakdown of lens tissue at the beam focus to reduce Young's modulus of the tissue.

15. The ophthalmic laser surgery system of claim 14, wherein the pulsed laser beam focused inside the lens has a pulse duration of 8 fs to 51 fs and a photodisruption threshold pulse energy of 36 nJ to 90 nJ.

16. The ophthalmic laser surgery system of claim 14, wherein the laser source includes a femtosecond laser, and a pulse picker configured to perform fast-blanking of laser pulses generated by the femtosecond laser.

17. The ophthalmic laser surgery system of claim 16, wherein the laser source further includes a pulse compressor configured to generate an original pulsed laser beam having a pulse duration of less than 200 fs, and a group velocity dispersion pre-compensation device configure to perform group velocity dispersion pre-compensation of the original pulsed laser beam so that the pulsed laser beam focused to the lens has a pulse duration of less than 200 fs.

18. The ophthalmic laser surgery system of claim 17, wherein the laser beam delivery optical system includes two-stage polarization attenuator, comprising a first attenuator, which is set to a fixed value of attenuation, and a second, variable attenuator, and the second attenuator including a half-wave plate and a polarization beam splitter.

19. The ophthalmic laser surgery system of claim 14, wherein the laser beam delivery optical system includes a beamsplitter configured to direct a portion of a laser beam reflected from the lens tissue to a light detector to detect photodisruption of the tissue.

20. The ophthalmic laser surgery system of claim 14, wherein the laser beam delivery optical system includes a variable aperture configured to adjust a numerical aperture of the pulsed laser beam, and wherein the laser beam delivery optical system is configured to scan the pulsed laser beam having a first numerical aperture in an anterior and center portion of the lens, and to scan the pulsed laser beam having a second numerical aperture which is lower than the first numerical aperture in a posterior and peripheral portion of the lens.

21. The ophthalmic laser surgery system of claim 14, wherein the laser beam delivery optical system is configured to scan the pulsed laser beam at oblique incidence angles in the lens.

22. The ophthalmic laser surgery system of claim 14, further comprising an optical coherence tomography subsystem configured to generate images of the lens tissue, and wherein the laser beam delivery optical system includes a beam combiner configured to combine an OCT sample beam and the pulsed laser beam into a common optical path.

23. An ophthalmic laser surgery system for treating presbyopia of a crystalline lens of a patient's eye, the system comprising:

a laser source configured to generate a pulsed laser beam comprising a plurality of laser pulses; and a laser beam delivery optical system configured to focus the pulsed laser beam into a beam focus inside the lens and to scan the pulsed laser beam in the lens according to a treatment pattern, wherein a numerical aperture NA of the laser beam is between 0.125 and 0.2, a pulse duration $\tau$ of the laser pulses in the lens is from 8 fs to 51 fs, and a photodisruption threshold pulse energy $E_0$ of the laser pulses in the lens is from 36 nJ to 90 nJ, and wherein the pulsed laser beam induces optical breakdown of lens tissue at the beam focus to reduce Young's modulus of the tissue.

24. The ophthalmic laser surgery system of claim 23, wherein the pulse duration r and the pulse energy E satisfy a relationship:

$$\tau \leq 3.157\ n \cdot NA^2 \cdot E / (c \cdot \lambda^2)$$

where n is a refractive index of the tissue, c is the speed of light (c=0.3 μm/fs), and A (in unit μm) is a wavelength of the pulsed laser beam.

25. The ophthalmic laser surgery system of claim 23, wherein the laser source includes a femtosecond laser, and a pulse picker configured to perform fast-blanking of laser pulses generated by the femtosecond laser.

26. The ophthalmic laser surgery system of claim 25, wherein the laser source further includes a pulse compressor configured to generate an original pulsed laser beam having a pulse duration of less than 200 fs, and a group velocity dispersion pre-compensation device configure to perform group velocity dispersion pre-compensation of the original pulsed laser beam so that the pulsed laser beam focused to the lens has a pulse duration of less than 200 fs.

27. The ophthalmic laser surgery system of claim 26, wherein the laser beam delivery optical system includes two-stage polarization attenuator, comprising a first attenuator, which is set to a fixed attenuation, and a second, variable attenuator, the second attenuator including a half-wave plate and a polarization beam splitter.

28. The ophthalmic laser surgery system of claim 23, wherein the laser beam delivery optical system includes a beamsplitter configured to direct a portion of a laser beam reflected from the lens tissue to a light detector to detect photodisruption of the tissue.

29. The ophthalmic laser surgery system of claim 23, wherein the laser beam delivery optical system includes a variable aperture configured to adjust a numerical aperture of the pulsed laser beam, and wherein the laser beam delivery optical system is configured to scan a pulsed laser beam having a first numerical aperture in an anterior and center portion of the lens, and to scan a pulsed laser beam having a second numerical aperture which is lower than the first numerical aperture in a posterior and peripheral portion of the lens.

30. The ophthalmic laser surgery system of claim 23, wherein the laser beam delivery optical system is configured to scan the pulsed laser beam at oblique incidence angles in the lens.

31. The ophthalmic laser surgery system of claim 23, further comprising an optical coherence tomography subsystem configured to generate images of the lens tissue, and wherein the laser beam delivery optical system includes a beam combiner configured to combine an OCT sample beam and the pulsed laser beam into a common optical path.

* * * * *